United States Patent
Schmitt

(10) Patent No.: US 11,946,942 B2
(45) Date of Patent: Apr. 2, 2024

(54) DEVICE FOR TABLETING A POWDER, LIQUID, PASTE, ENCAPSULATED OR GRANULAR ACTIVE INGREDIENT COMPOSITION

(71) Applicant: Fritz Schmitt, Luxembourg (LU)

(72) Inventor: Fritz Schmitt, Luxembourg (LU)

(73) Assignee: LUXCAN INNOVATION S.A., Luxembourg (LU)

( * ) Notice: Subject to any disclaimer, the term of this patent is extended or adjusted under 35 U.S.C. 154(b) by 399 days.

(21) Appl. No.: 17/421,062

(22) PCT Filed: Dec. 10, 2019

(86) PCT No.: PCT/DE2019/101067
§ 371 (c)(1),
(2) Date: Jul. 7, 2021

(87) PCT Pub. No.: WO2020/143864
PCT Pub. Date: Jul. 16, 2020

(65) Prior Publication Data
US 2022/0062108 A1 Mar. 3, 2022

(30) Foreign Application Priority Data

Jan. 7, 2019 (DE) .................... 10 2019 000 016.1
Jan. 7, 2019 (DE) .................... 10 2019 000 018.8
Jan. 15, 2019 (DE) .................... 10 2019 000 199.0

(51) Int. Cl.
*A61J 3/10* (2006.01)
*A24F 7/04* (2006.01)
(Continued)

(52) U.S. Cl.
CPC ............. *G01N 33/948* (2013.01); *A24F 7/04* (2013.01); *A24F 40/30* (2020.01); *A24F 40/42* (2020.01);
(Continued)

(58) Field of Classification Search
CPC ... A61J 3/10; B30B 11/04; B30B 15/302–306
See application file for complete search history.

(56) References Cited

U.S. PATENT DOCUMENTS

2004/0172169 A1* 9/2004 Wright, IV .......... A61K 9/5078
700/265
2012/0061869 A1* 3/2012 Boeckx ................. B29B 7/726
425/110
(Continued)

FOREIGN PATENT DOCUMENTS

EP 2532349 A1 12/2012
EP 2937206 A1 10/2015
(Continued)

OTHER PUBLICATIONS

International Search Report (English and German) and Written Opinion (German) of the International Searching Authority issued in PCT/DE2019/101067, dated Apr. 6, 2020; ISA/EP.

*Primary Examiner* — Mary Lynn F Theisen
(74) *Attorney, Agent, or Firm* — Harness, Dickey & Pierce, P.L.C.

(57) ABSTRACT

The invention relates to a device for tabletting a powdered, liquid, pasty, encapsulated or granular active ingredient composition, having a magazine which has a plurality of active ingredient containers each with an individually controllable dosing device and a nozzle for the active ingredient outlet, wherein the magazine is adjustable between a plurality of setting positions relative to at least one die chamber, wherein in each of the setting positions at least one of the nozzles faces an opening of the die chamber. A corresponding method is further described.

19 Claims, 4 Drawing Sheets

Figure 1:
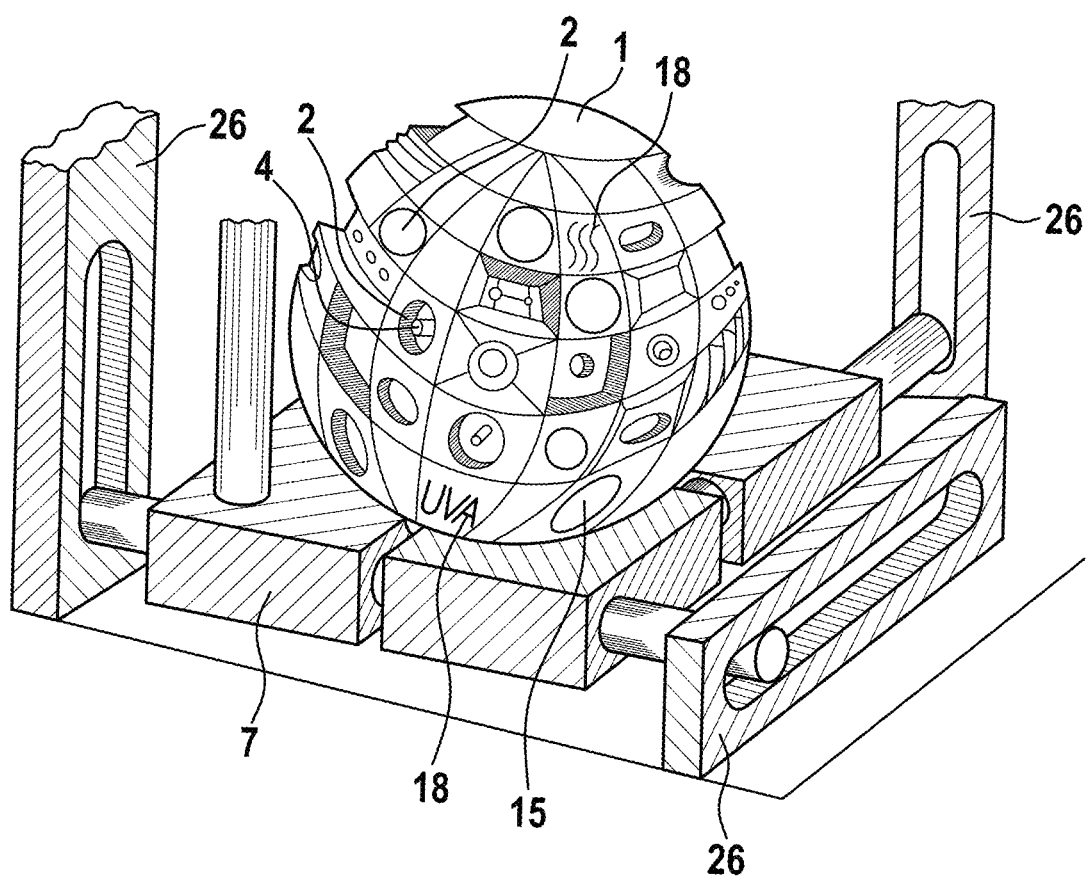

(51) Int. Cl.
- *A24F 40/30* (2020.01)
- *A24F 40/42* (2020.01)
- *A24F 40/465* (2020.01)
- *A24F 40/51* (2020.01)
- *A24F 40/57* (2020.01)
- *A24F 42/10* (2020.01)
- *A61K 36/185* (2006.01)
- *A61M 11/02* (2006.01)
- *A61M 11/04* (2006.01)
- *A61M 15/00* (2006.01)
- *B01L 3/00* (2006.01)
- *B30B 11/04* (2006.01)
- *B30B 15/30* (2006.01)
- *G01N 33/52* (2006.01)
- *G01N 33/94* (2006.01)

(52) U.S. Cl.
CPC ............ *A24F 40/465* (2020.01); *A24F 40/51* (2020.01); *A24F 40/57* (2020.01); *A24F 42/10* (2020.01); *A61J 3/10* (2013.01); *A61K 36/185* (2013.01); *A61M 11/02* (2013.01); *A61M 11/047* (2014.02); *A61M 15/0021* (2014.02); *A61M 15/0028* (2013.01); *B01L 3/502* (2013.01); *B01L 3/52* (2013.01); *B01L 3/523* (2013.01); *B30B 11/04* (2013.01); *B30B 15/302* (2013.01); *G01N 33/52* (2013.01); *A61M 11/041* (2013.01); *A61M 2205/3368* (2013.01); *A61M 2205/3686* (2013.01); *A61M 2205/6054* (2013.01); *A61M 2205/6072* (2013.01); *A61M 2205/609* (2013.01); *A61M 2205/75* (2013.01); *A61M 2206/20* (2013.01); *B01L 2300/069* (2013.01); *B01L 2300/0835* (2013.01); *B01L 2300/168* (2013.01); *B01L 2300/1816* (2013.01)

(56) References Cited

U.S. PATENT DOCUMENTS

| | | | |
|---|---|---|---|
| 2012/0207867 A1* | 8/2012 | Mercado | B30B 11/06 425/149 |
| 2013/0034633 A1 | 2/2013 | Von Hasseln | |
| 2013/0292884 A1* | 11/2013 | Anderson | A61J 3/10 264/491 |
| 2015/0374586 A1* | 12/2015 | Gamlen | B30B 11/14 425/150 |
| 2018/0271791 A1* | 9/2018 | Myerson | A61J 3/10 |
| 2019/0159970 A1 | 5/2019 | Franck | |
| 2020/0261653 A1 | 8/2020 | Schmitt | |
| 2020/0353171 A1 | 11/2020 | Schmitt | |
| 2020/0360611 A1 | 11/2020 | Schmitt | |

FOREIGN PATENT DOCUMENTS

| | | |
|---|---|---|
| WO | WO-0187272 A2 | 11/2001 |
| WO | WO-2010151302 A1 | 12/2010 |
| WO | WO-2011117012 A1 | 9/2011 |
| WO | WO-2017075096 A1 | 5/2017 |
| WO | WO-2017175057 A1 | 10/2017 |

* cited by examiner

DEVICE FOR TABLETING A POWDER, LIQUID, PASTE, ENCAPSULATED OR GRANULAR ACTIVE INGREDIENT COMPOSITION

CROSS-REFERENCE TO RELATED APPLICATIONS

This application is a U.S. National Phase Application under 35 U.S.C. 371 of International Application No. PCT/DE2019/101067, filed on Dec. 10, 2019, which claims the benefit of German Application No. 10 2019 000 0199.0, filed on Jan. 15, 2019, and German Application No. 10 2019 000 016.1, filed on Jan. 7, 2019, and German Application No. 10 2019 000 018.8, filed on Jan. 7, 2019. The entire disclosures of the above applications are incorporated herein by reference.

BACKGROUND

This section provides background information related to the present disclosure which is not necessarily prior art.

Technical Field

The invention relates to a device as well as a method for tabletting a powdered, liquid, pasty, encapsulated or granular active ingredient composition. In particular, a device as well as a method for the production of a powdery, liquid, pasty, encapsulated or granular single-dose active ingredient form are described, wherein at least a portion of the composition may contain active ingredients from the hemp plant (cannabis).

Discussion

Known are tablets that are manufactured under press pressure from powders, granules or other active ingredient precursors on tablet presses. Tablets can have different shapes. In the case of tablets for oral use, the biconvex form is particularly common. Tablets for medicinal use are considered to be medicinal products for other health-related uses and are classified as medical devices or dietary supplements. Tablets are also used in other areas. Among the pharmaceutical forms, tablets play a special role with a share of almost 50%.

Large quantities of tablets go unused each year because they cannot be consumed before the expiration date due to excessive packaging. It is estimated that 30% of all prescribed medications are disposed of unused.

In addition, medications are still prescribed today as if all patients had identical biological prerequisites for therapy. However, in order to achieve better treatment successes, medical progress increasingly demands that individual patient characteristics are also taken into account when prescribing medication and that tailored therapies are offered. Similarly, in many cases, sparing dosing of medications compared to standard medication is sufficient, which also reduces the risk of side effects. There is therefore a high demand for individualized medication, particularly in tablet form.

3D printers are also known from the prior art, for example, from their use in food technology. In this process, a food component is often brought into a desired three-dimensional shape in a flowable state and then cured. To date, such processes have been used, for example, in the production of molds made of chocolate and the like. For example, WO 2011/117012 A1 describes the selective application of food supplements to food products. US 2013/0034633 A1 describes a system for producing a freely molded three-dimensional food product. Furthermore, a method is described by means of which certain properties of a manufactured food product can be varied.

EP 2 937 206 A1 describes a process for the production of chocolate-based food products in which the chocolate is cured after the dosing process to serve as a crystallization initiator for a subsequent layer. The solid chocolate is intended to form a complete internal and external three-dimensional structure of the food product, into which liquid or gaseous substances can be incorporated in internal chambers of the structure with solid walls.

WO 2010/151302 A1 discloses a method for printing foodstuffs in which small drops of a liquid foodstuff and a liquid binder, preferably consisting of a gelling agent that solidifies when pressure is applied, are processed.

US 2013/0034633 A1 shows a manufacturing process for a three-dimensional food product, in which local solidification is brought about in a powder layer by localized application of liquid droplets using liquid and powder. Through the application of further powder layers and structures of liquid drops, a three-dimensional food structure is formed after the removal of non-solidified powder components.

SUMMARY

This section provides a general summary of the disclosure, and is not a comprehensive disclosure of its full scope or all of its features.

It is therefore one aspect of the invention to provide a device and method for tableting drug compositions that are highly flexible to adapt to changing drug compositions and are scalable.

Accordingly, a device for tabletting a powdered, liquid, pasty, encapsulated or granular active ingredient composition is proposed, comprising a magazine having a plurality of active ingredient containers each with an individually controllable dosing device and a nozzle for the active ingredient outlet. The magazine is adjustable between a plurality of set positions relative to at least one die chamber, wherein in each of the set positions at least one of the nozzles faces an opening of the die chamber.

The magazine can be spherical. The active ingredient containers can extend in the radial direction of the magazine and open with their respective nozzle into a spherical surface of the magazine. It may be provided that the active ingredient(s) held in the active ingredient container are stored in the active ingredient container fluidically separated from the environment of the device. The active ingredient containers may at least partially comprise a temperature control device to maintain an active ingredient held in one of the active ingredient containers at a predetermined temperature or to bring it to a specific temperature prior to dispensing into the die chamber, which promotes a chemical transformation of the active ingredient or alters a physical property of the active ingredient.

The at least one die chamber can be accommodated in a base plate, which has a concave recess in which the spherical magazine is accommodated. The at least one die chamber can be arranged at a deepest point of the recess.

The magazine may be adjustable relative to the base plate about at least one axis extending parallel to the base plate.

The spherical magazine can have a cavity in its center in which a spherical actuating element is accommodated in a freely movable and form-fitting or at least approximately form-fitting manner. In this context, the actuating element can have an actuator that can be adjusted between an actuating position and a release position. The actuating element may have an eccentric center of gravity arranged along a linear adjustment direction of the actuator between the actuating position and the release position.

The spherical actuator may have a passage extending through its center in which a solenoid coil with a coil core movable along the coil axis is disposed.

The passage may be positioned with respect to the center of gravity of the spherical confirmation element such that the passage is oriented vertically regardless of the orientation of the magazine.

The magazine may have a linearly adjustable punch that faces the opening of the die chamber in one of the set positions or in another set position of the magazine relative to the die chamber.

The punch may have a punch die at a free end, with the punch in an extended position projecting over the opening into the die chamber and with the punch in a release position out of engagement with the die chamber.

At least one of the active ingredient containers may comprise a processing device for an active ingredient. The processing device may be or include a heating element for heating and/or a cooling element for cooling an active ingredient.

In addition to the plurality of active ingredient containers, the magazine can have at least one carrier material container with an individually controllable dosing device and a nozzle for the carrier material outlet. Thereby, in a further position of the magazine, the nozzle of the carrier material container can face an opening of the die chamber and/or a base plate of the device, which has the die of a tablet packaging.

The die may have a plurality of the die chambers, preferably arranged in a regular grid.

The method for tableting an active ingredient with a device of the type previously described may comprise the steps of:
 a) Specifying a drug composition to be tableted;
 b) moving the magazine relative to the die chamber until the magazine assumes a position in which the active ingredient container of the magazine faces the die chamber with its nozzle, in which an active ingredient of the active ingredient composition is stored;
 c) dosing a dose of the first active ingredient predetermined by the active ingredient composition into the die chamber; and
 d) optionally repeating steps b) and c) for each additional active ingredient of the active ingredient composition if the active ingredient composition has more than one active ingredient.

The method may have the following further steps:
 e) moving the magazine relative to the die chamber until the magazine assumes a position in which a binder supply container of the magazine faces the die chamber with its nozzle in which a binder is stored;
 f) Dosing a dose of the binder predetermined by the active ingredient composition into the die chamber.

Further, the method may comprise the following steps:
 g) moving the magazine relative to the die chamber until the magazine assumes a position in which a linearly adjustable punch of the magazine, which has a punch die at a free end, faces an opening of the die chamber;
 h) displacing the punch from a release position, in which the punch with its punch die is out of engagement with the die chamber, into an extended position, in which the punch with its punch die projects into the die chamber via the opening, wherein the at least one active ingredient metered into the die chamber and optionally a binder are compacted.

Likewise, the method may further comprise the steps of:
 i) moving the magazine relative to the die chamber until the magazine assumes a set position in which a carrier material container of the magazine, in which a carrier material is stored, faces the die chamber and/or a base plate having the die of a tablet package with its nozzle; and
 j) Metering the carrier material into the die chamber and/or the die of the base plate.

Dispensing the carrier material into the die chamber may include forming an active ingredient capsule. The dispensing of the carrier material into the die of the base plate may include the formation of a tablet package.

The process described can be used to produce a child-resistant blistery er packaging or a wraparound packaging for an active ingredient or an active ingredient tablet. In particular, the process enables the production of the tablet, the production of the package, and any necessary labeling of the package and possibly the addition of a data carrier to the package to provide content information and the like to all be provided in a single operation.

The device described above and the process for tableting active ingredients can make use of the principles of additive manufacturing known from the prior art, for example 3D printing. This refers to all manufacturing processes in which solids can be applied layer by layer and three-dimensional objects can subsequently be produced. The layer-by-layer build-up is usually computer-controlled using at least one liquid or solid material. The active ingredient containers can be designed in the manner of printer cartridges and each have a dosing device that can be individually controlled. This ensures that contact between the different active ingredients in the device is precluded. The nozzles of the active ingredient containers can, for example, be replaceable in the same way as disposable cannulas and can be replaced after each use of the device according to the invention or application of the process according to the invention.

Advantageously, the applied active ingredient doses or active ingredient layers are compacted or compressed after all the individual doses or layers have been metered. This can be done in a similar way to prior art compression using a punch and a die. The die is formed by the die chamber. The punch can be held in the magazine and, for compression or compaction, the magazine can be brought into a position in which the punch is aligned with the die chamber, so that the punch can be extended from the magazine and inserted into the die chamber, for example by linear adjustment. Advantageously, an underside of the die chamber is also designed as a movable die, so that when compacting or compacting the metered active ingredients in the die chamber, the two dies are brought closer to each other, whereby homogeneous compaction is achieved. Known automatic devices for compacting tablets have a vertically aligned lower punch, which runs in a die, and an upper punch, which is inserted into the die only for compression. In contrast, the device according to the invention can provide for the tablet blank to be metered or printed directly into the die chamber and, if necessary, only an upper punch, which is held in the magazine, to be inserted into the die for further compression. The thickness, strength and gloss of the tablet thus depend solely on the upper die and its compression pressure.

The insertion depth and the pressure strength of the upper punch into the die chamber and the pressure strength can be regulated with the shaping of the blank deposited or metered in the die chamber. The lower punch can be arranged in the die and limit the filling space of the die chamber downward. During the compaction process, it forms the counter-bearing for the upper punch held in the magazine. After completion of the compaction process, the lower punch is moved upwards, displacing the tablet onto the edge of the die, where it can be pushed aside. In an optional next work step, the tableted active ingredient can be impregnated with an active ingredient or coated with a protective or functional layer.

The active ingredient containers can be designed as exchangeable cartridges. In one embodiment of the invention, a carrier material for the production of a tablet package can be provided in one of the active ingredient containers or in one of the cartridges, for example for the formation of a blister pack, for which purpose, for example, a biodegradable material can be provided, for example silicone.

The process according to the invention can be carried out under clean room conditions, for which the device according to the invention can have an air circulation system with HEPA filters. The sterilizability of the device may be ensured by a UV or ozone system or by any other system. The device and method according to the invention can be used to control individual compositions of active ingredients and formulations of tablets. Using patient-related data, tablets can be produced cost-effectively within a few minutes, even in small quantities.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
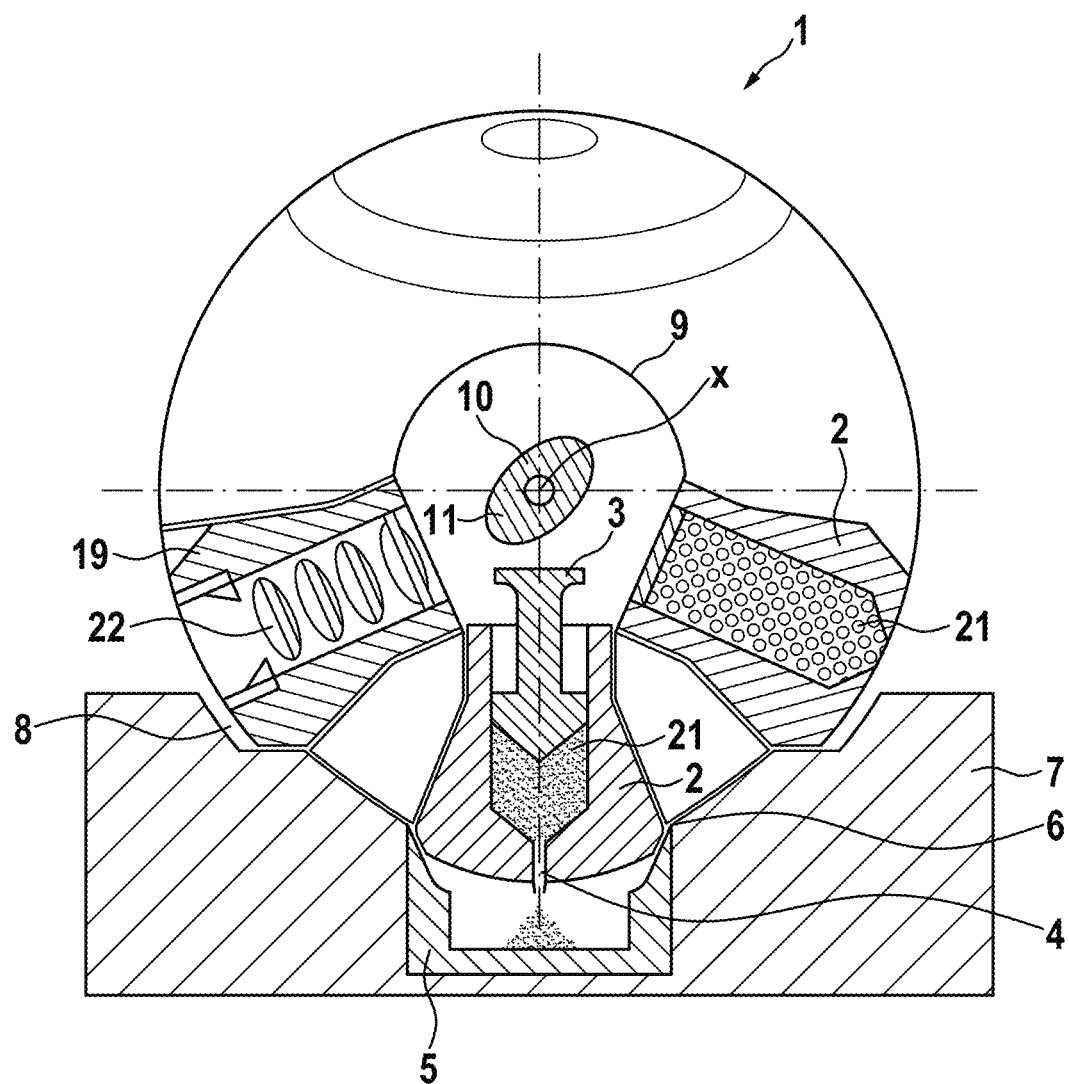
Figure 3:
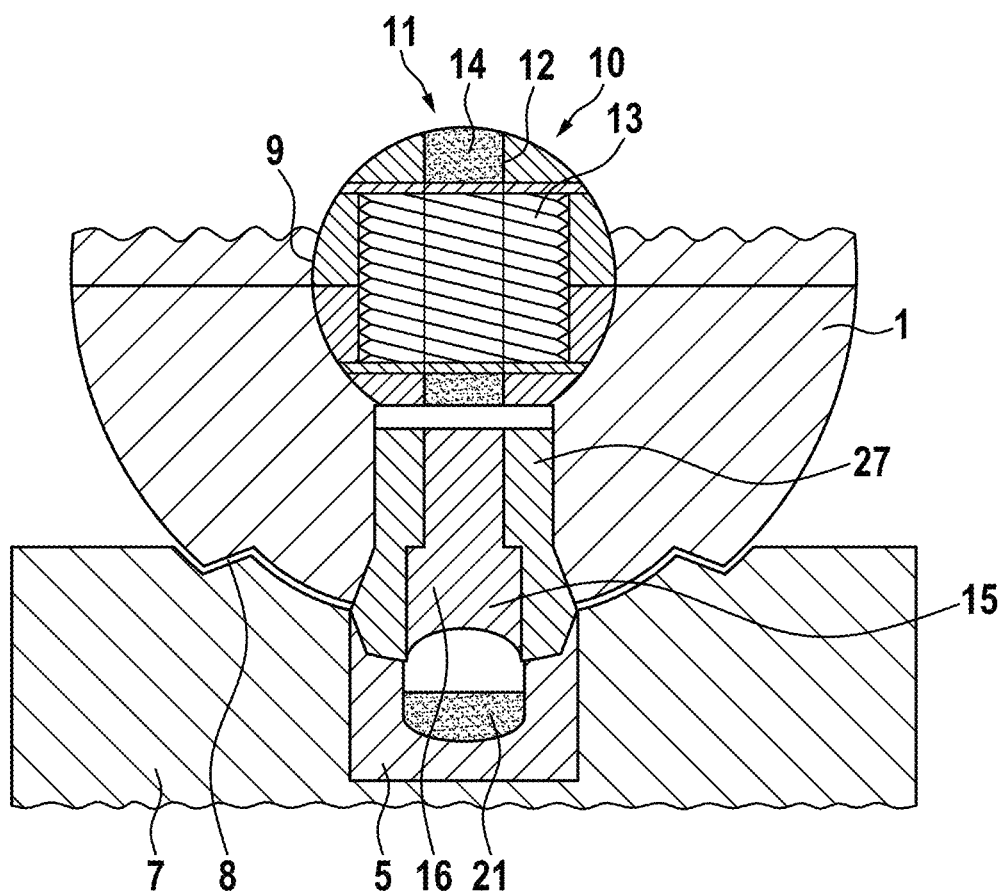
Figure 4:
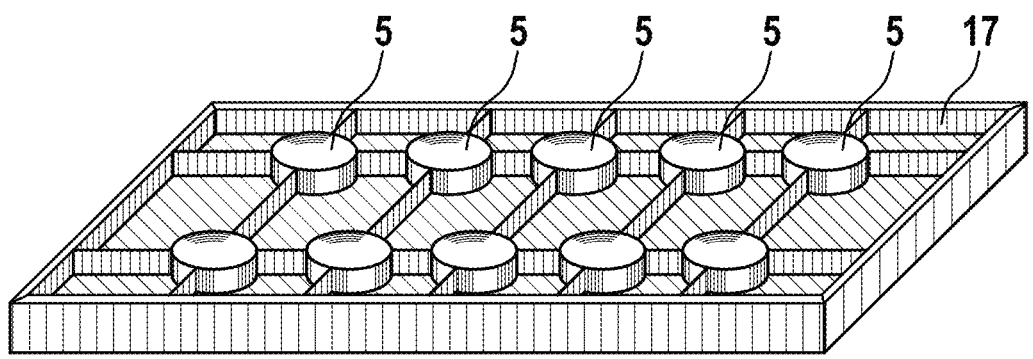
Figure 5:
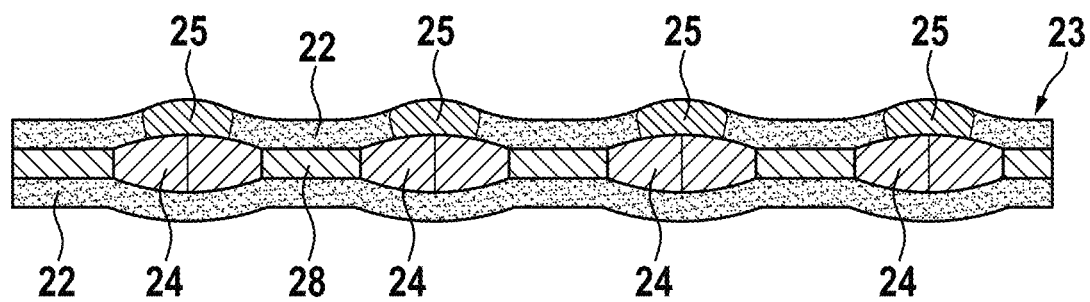

Further details of the invention are explained with reference to the figures below. Thereby shows:

FIG. 1 a perspective and schematic diagram of an exemplary embodiment of a device according to the invention;

FIG. 2 a cross-section and schematic representation of a further embodiment of a device according to the invention;

FIG. 3 in cross-section and in schematic representation a detail of a further embodiment of a device according to the invention;

FIG. 4 a perspective and schematic view of a base plate according to one embodiment of the invention; and FIG. 5 in cross-section and in schematic representation an embodiment of a tablet packaging.

DETAILED DESCRIPTION

Example embodiments will now be described more fully with reference to the accompanying drawings.

FIGS. 1 and 2 each show exemplary embodiments of a device according to the invention for tableting an active ingredient composition. The features of the two n embodiments shown can also be implemented in a single embodiment.

The individual active ingredients of the active ingredient composition can be separated from one another in the magazine 1 of the device, in particular fluidically separated from one another, for example as powdered, liquid, pasty, encapsulated or granular active ingredients in a respective active ingredient container 2. Accordingly, the magazine 1 has a plurality of active ingredient containers 2, in each of which an active ingredient or a defined active ingredient mixture is provided, each of the active ingredient containers 2 having a separately controllable dosing device 3. The active ingredient containers 2 can furthermore have a nozzle 4 for the active ingredient outlet.

The magazine 1 is spherical in shape, so that the active ingredient containers 2 extend in the radial direction of the magazine 1 and open with their respective nozzle 4 into a spherical surface of the magazine 1. The spherical magazine 1 can be adjustable between a plurality of setting positions relative to at least one die chamber 5 in the base plate 7, wherein in each of the setting positions at least one of the active substance containers 2, in particular the respective nozzle 4 of the respective active substance container 2, faces an opening 6 of the die chamber 5, so that when the dosing device 3 is actuated the active substance held in the respective active substance container 2 can be metered into the die chamber 5.

The dosing device 3 can have suitable means for the process-reliable delivery of a predetermined dose into the chamber 5, for example a flow meter, a weight sensor or the like.

In addition to the plurality of active ingredient containers 2, the magazine 1 can have further functional elements that can come into contact with the die chamber 5 or an active ingredient composition stored therein via the spherical surface of the magazine 1. For example, one of the functional elements may be a means for compacting the active ingredient composition in the die chamber 5, such as a punch with a die. In addition, the magazine 1 may comprise at least one carrier material container 19 in which at least one carrier material 22 is provided which can be applied to the die chamber 5 as required, for example to form an active ingredient capsule containing the active ingredient composition.

As can be further seen from FIG. 2, the at least one die chamber 5 received in the base plate 7 may be arranged in a concave recess 8 of the base plate 7, preferably at a deepest point of the recess 8, wherein the spherical magazine 1 is held in the concave recess 8. The spherical magazine 1 may be at least partially positively received in the recess 8, so that the magazine 1 is guided in the recess 8 when it changes its orientation.

FIG. 2 further shows that the spherical magazine 1 has a cavity 9 in its center, in which an actuating element 10 is freely received. The actuating element 10 can be designed in particular as a rotatably mounted cam, wherein an axis of rotation x of the actuating element 10 is located outside the center of gravity of the actuating element 10. Since the actuating element 10 is freely rotatably accommodated in the cavity 9, it can always be located with its center of gravity at a lowest point, irrespective of the orientation of the magazine 1 with respect to the base plate 7, and can, for example, be brought into engagement with a dosing device 3 which is brought into alignment with the die chamber 5 at a lowest point of the spherical magazine 1. In this way, it can be achieved that with the rotation of the magazine 1, wherein a particular active substance container 2 in which a particular active substance 21 is held is brought to the lowermost position, the dosing device 3 of the particular active substance container 2 is actuated due to the gravity-driven actuating element 10.

In the embodiment according to FIG. 2, the dosing device is designed in the manner of a plunger, which is driven further into the active substance container 2 by the actuating element when the magazine 1 is displaced in the manner described above, as a result of which the active substance 21 reserved in the container 2 is dosed into the die chamber 5 via the nozzle 4 of the active substance container 2, which opens into the die chamber 5.

FIG. 3 shows a further embodiment of a magazine 1 according to the invention, wherein the magazine 1 is aligned with respect to the die chamber 5 in the base plate 7 in such a way that a punch 15 with a punch die 16 arranged at the end can be brought into engagement with the die chamber 5, for example in order to achieve compaction, compacting, shaping or other mechanical consolidation of the active substance 21 contained in the die chamber 5. The stamper 15 may serve, for example, to further tablet the active ingredient 21. However, according to the invention, stamping the active ingredient 21 with the stamp 15 is merely a variant for tabletting the active ingredient 21. As has already been described with reference to FIGS. 1 and 2, metering the active ingredient 21 or the active ingredients 21 into the die chamber 5 can also cause the active ingredient 21 to assume the contour of the die chamber 5 and, to that extent, to be tabletted.

For the solidification of the active ingredient in the die chamber, whether using the plunger 15 for compacting or another mechanical aid, a binder may be added to the active ingredient 21, as is known in principle from the prior art. The binder may be kept in a separate active ingredient container 2 of the magazine 1 and added to the active ingredient composition 21 in the die chamber 5 in a separate metering step, or may already be admixed to the active ingredients 21 or at least some of the active ingredients 21 in the active ingredient containers 2 of the magazine 1.

FIG. 3 also shows a further embodiment of an actuating element 10, which is arranged in the cavity 9 in the center of the spherical magazine 1. In this embodiment, in contrast to the embodiment according to FIG. 2, the actuating element 10 is also spherical in shape and is accommodated in the cavity 9 in a substantially form-fitting, but again freely movable manner. The actuating element 10 has a linearly adjustable actuator 11 which, in the representation according to FIG. 3, can be adjusted in the vertical direction between an actuating position and a release position.

The actuating element 10 has a passage 12 extending through its center, in which a solenoid coil 13 with a coil core 14 moving along the coil axis is located. The coil core 14 is rod-shaped and extends through the center of both the magazine 1 and the actuating element 10. The rod-shaped coil core 14 can be, for example, a permanent magnet which can be displaced along the coil axis by applying current to the coil. In FIG. 3, the coil core 14 is shown in its release position, in which the coil core 14 is not engaged with the plunger 15. By applying current, the bobbin core 14 can be displaced from the position shown in FIG. 3 to an actuation position in which it is displaced vertically downward relative to the release position and engages the plunger 15. In particular, the coil core can enter the linear guide 27 of the plunger 15 for this purpose, as a result of which the plunger 15 is driven with its end-side die 16 further into the die chamber 5 in order to tablet the active ingredient 21 or an active ingredient mixture, which may also have a binder in addition to at least one active ingredient, located in the die chamber 5. Subsequently, by reversing the current flow, the coil core 14 can be transferred back to the release position shown in FIG. 3.

FIG. 4 shows an exemplary embodiment of a die 17 as provided for forming a plurality of tablets and, at the same time, of a tablet package in which the tablets produced are packaged. For this purpose, the die 17 has a plurality of die chambers 5 arranged in a regular grid, so that, in addition to the production of the tablets in the die chambers 5 with the aid of the device according to the invention, for example one of the devices shown in FIGS. 1 to 3, carrier material can also be introduced into the die 17 in addition to the tablets 24, so that packaged tablets 24 can be produced.

FIG. 5 shows a cross-section through an exemplary embodiment of a tablet package 23 with tablets 24 accommodated therein, which has been produced with the aid, for example, of the device shown in FIGS. 1 to 4. Accordingly, the tablet package 23 has, in cross-section, a layer sequence comprising a lower carrier material layer 22 on which, in addition to the tablets 24, separating elements 28 separating the tablets 24 from one another are further arranged. Above the tablets 24 and the separating elements 28, a further carrier material layer 22 is formed with closures 25 embedded therein above each tablet 24.

All of the elements 22, 23, 24, 25, 28 shown in FIG. 5 can be produced with the aid of the device according to the invention in a corresponding printing process. For example, with the device shown in FIG. 1, using the die shown in FIG. 4, a continuous, i.e. uninterrupted, carrier material layer 22 can be introduced into the die 17 in a first process step, the carrier material 22 can, for example, be a plastic material. After the carrier material layer 22 has been introduced into the die 17 and, if necessary, hardened, in a next step the same device 1 can be used to form the tablets 24 as required by the patient in the die chambers 5 and above the carrier material layer 22 already hardened therein, as explained with reference to the preceding figures, for example. Analogously to the carrier material layer 22, the separating elements 28 can be deposited between the tablets 24. Subsequently, the closures 25 are formed above the tablets 24 and, in a final step, the die 17 is completely filled with carrier material 22 around the closures 25. All applications of the aforementioned active ingredients and other materials, including the carrier materials 22, the materials for the closures 25 and the separating elements 28 can be produced using one of the devices shown in FIGS. 1 to 3.

The dosing of the active ingredients and other substances can be carried out according to the principle of 3D printing. Thus, according to one embodiment, the invention may be realized as an automatic device for the production of tablets based on the principle of 3D printing, also known as additive manufacturing, additive manufacturing generative manufacturing or rapid technologies.

The layer-by-layer build-up can be computer-controlled from one or more liquid or solid active ingredients and at least one binder. The active ingredients and the binder are stored in active ingredient containers in the form of print cartridges, each of which has a dosing device and can be controlled individually. This ensures that the active ingredients cannot come into contact with each other.

The nozzles on the printer cartridges can be replaceable in a similar way to bucket nozzles and are replaced after each printing process. One particular embodiment provides for the tabletting material to be pressed into a tablet after 3D printing using the same device with the aid of a single pressing process. For this purpose, two movable punches can be provided as pressing tools. Known automatic devices for the production of tablets have a vertically aligned lower punch, which runs in a die, and an upper punch, which is inserted into the die only for pressing. In one embodiment of the invention, the tablet blank is printed directly in the die chamber and then the upper punch slides into the die, pressing the tablet. The thickness, strength and press gloss of the tablet depend on its geometry and pressing pressure. The insertion depth and the pressure strength can be regulated with the shaping of the 3D blank. The lower punch can be located inside the die. It limits the filling space downwards. During the pressing process, it usually forms the counter-bearing. When pressing is complete, it can be moved upwards, thus bringing the tablet to the edge of the die, where it can be pushed aside. In the next cycle, if the blank is made of absorbent material, it can be impregnated with active ingredients or coated with a protective or functional layer. The layer can have the following properties.

The magazine can have several exchangeable cartridges and, in a particular embodiment of the invention, it is envisaged to use the same magazine and the same device to replace the otherwise usual blistering of tablets. A biodegradable material may be provided for this purpose, for example silicone. The complete process can be carried out in a construction space of the device, which is hermetically sealed. A recirculating air system with HEPA filters ensures clean room conditions. The device can be sterilized by UV or ozone treatment, or by other suitable systems.

The greatest advantage of the invention lies in the individually controllable composition of the active ingredients and shaping of the tablets. Due to the controllability of the device and the feeding of patient-related data, tablets can be produced cost-effectively within a few minutes, even in small quantities.

In addition to the at least one die chamber, the base plate can have pressing devices with a further die in the form of a tablet and/or holding devices for tablet blanks, cartridges, ampoules, or syringe bodies. Likewise, the active ingredient containers of the magazine can be designed as printer cartridges or cartridges which, for example, can not only contain and dose active ingredients, but can also be set up to be able to press them into a die at up to 80 kN/cm3, for example by having a punch with a die at the end.

One embodiment of the invention relates to a 3D drug dosing device comprising an exchangeable unit and a permanently installed unit. The interchangeable unit has active ingredients and possibly other substances in the form of powder, particles, fluid or the like in each case in a suitable reservoir, which can be provided in the form of a pressurized pressure cartridge for holding the active ingredient or the other substance.

In contrast to conventional tabletting machines, the magazine can be designed not as a fixed pressing device, but as a vertically and horizontally aligned device that can be moved in the X, Y and Z directions. This measure also allows 3D molded blanks to be produced from carrier material for active ingredients without the need for compression molds. The blanks can also be shaped with pressing tools. The dosing devices can also be used only to fill the pressing tools or hollow bodies that have been previously printed in the same system. The hollow bodies can be made of absorbent sponge/foam material that is highly absorbent, e.g. silica, hyaluronic acid or substances that readily form a compound with the active ingredients.

The dosing device may comprise a sensor for detecting the flow rate of a liquid active ingredient or binder, a fluid channel provided with a flow resistance and fluidly connected to the active ingredient reservoir, and at least one nozzle connected to the fluid channel.

Concave dies can be attached to a spherical surface of the magazine, which can shape active substances into a desired form. It has proved particularly advantageous to freely move the spherical magazine in a part-spherical or hemispherical holder. The holder, in turn, can be movable in the X, Y and Z directions. The holder can have at least four rotatable drives that can rotate the magazine in all directions. This makes it possible to use all cartridges or tools located in the sphere in any plane in space. Contact surfaces on the surfaces and electromagnets to be activated guarantee safe adjustment.

A liquid drug contained in the drug container can preferably be pressurized with the aid of a constant pressure sensor. The device may have at least one pressure sensor to detect the pressure of the liquid medicament upstream of a flow resistance of the active ingredient container. Further, another pressure sensor may be provided downstream of the flow resistance, wherein a control device is adapted to control the flow rate of a liquid drug.

The dosing system can work according to the overpressure principle and preferably uses a micromechanically manufactured optical sensor and thus offers the possibilities of externally influencing the dosing rate via the control device to compensate for any defects on the printed tablet.

The dispensing system may include a pinch valve that is actuated by the control device in a timed manner to allow or prevent flow through a tube of the dispensing system. This pinch valve engages the tubing from the outside and squeezes it to prevent flow of the liquid medication. As a result, the valve does not come into contact with the drug. Thus, the valve can be a part of the permanent device.

The features of the invention disclosed in the foregoing description, in the drawings as well as in the claims may be essential to the realization of the invention both individually and in any combination.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A device for tabletting a powdery, liquid, pasty, encapsulated or granular active substance composition, with a magazine comprising a plurality of active substance containers each with an individually controllable dosing device and a nozzle for the active substance outlet, wherein the magazine is adjustable between a plurality of setting positions relative to at least one die chamber, wherein in each of the setting positions at least one of the nozzles faces an opening of the die chamber, wherein the magazine is a spherical magazine, and wherein the active ingredient containers extend in the radial direction of the spherical magazine and open with their respective nozzle into a spherical surface of the spherical magazine.

2. The device of claim 1, wherein the at least one die chamber is received in a base plate having a concave recess in which the spherical magazine is received.

3. The device of claim 2, wherein the at least one die chamber is disposed at a deepest point of the recess.

4. The device of claim 2, wherein the spherical magazine is adjustable relative to the base plate about at least one axis extending parallel to the base plate.

5. The device according to claim 1, in which the spherical magazine has, in its center, a cavity in which an actuating element is freely movably accommodated, the actuating element having an actuator which is adjustable between a confirmation position and a release position.

6. The device of claim 5, wherein either the actuating element is spherical in shape and is positively received in the cavity, or wherein the actuating element is a rotatably mounted cam with its center of gravity located outside the axis of rotation, wherein the actuator is a cam projection.

7. The device of claim 5, wherein the actuating member has a passage extending through its center in which is disposed a solenoid coil having a coil core movable along the coil axis.

8. The device of claim 7, wherein the passageway is positioned with respect to the center of gravity of the actuating member such that the passageway is vertically oriented regardless of the orientation of the magazine.

9. The device according to claim 1, wherein the spherical magazine comprises a linearly adjustable plunger facing the opening of the die chamber in one of the setting positions or in a further setting position of the spherical magazine relative to the die chamber.

10. The device of claim 9, wherein the plunger has a die at a free end thereof, with the plunger in an extended position projecting into the die chamber through the opening, and with the plunger in a release position out of engagement with the die chamber.

11. The device according to claim 1, wherein at least one of the active ingredient containers comprises processing means for an active ingredient.

12. The device of claim 11, wherein the processing means is or comprises a heating element for heating and/or a cooling element for cooling an active ingredient.

13. The device according to claim 1, in which the magazine has, in addition to the plurality of active substance containers, at least one carrier material container with an individually controllable dosing device and a nozzle for the carrier material outlet, wherein in a further setting position of the magazine the nozzle of the carrier material container faces an opening of the die chamber and/or a base plate of the device, which has the die of a tablet package.

14. The device of claim 13, wherein the die comprises a plurality of the die chambers.

15. A method for tableting an active ingredient with a device according to claim 1, comprising:
   a. Prescribing an active ingredient composition to be tableted;
   b. Adjusting the magazine relative to the die chamber until the magazine assumes a position in which the active substance container of the magazine faces the die chamber with its nozzle, in which an active substance of the active substance composition is stored;
   c. dosing a dose of the first active ingredient predetermined by the active ingredient composition into the die chamber; and
   d. optionally repeating steps b. and c. for each additional active ingredient of the active ingredient composition if the active ingredient composition comprises more than one active ingredient.

16. The method of claim 15, further comprising:
   e. Moving the magazine relative to the die chamber until the magazine assumes a position in which a binder reservoir of the magazine faces the die chamber with its nozzle, in which a binder is stored;
   f. Dosing a dose of the binder predetermined by the active ingredient composition into the die chamber.

17. The method of claim 15, further comprising:
   g. moving the magazine relative to the die chamber, until the magazine assumes a position in which a linearly adjustable plunger of the magazine, which has a die at a free end, faces an opening of the die chamber;
   h. displacing the plunger from a release position, in which the plunger with its die is out of engagement with the die chamber, into an extended position, in which the plunger with its die projects into the die chamber via the opening, the at least one active substance metered into the die chamber and, if appropriate, a binder being compressed.

18. The method of claim 15, further comprising:
   i. displacing the magazine relative to the die chamber until the magazine assumes a position in which a carrier material container of the magazine, in which a carrier material is stored, faces with its nozzle the die chamber and/or a base plate having the die of a tablet package; and
   j. Metering the carrier material into the die chamber and/or the die of the base plate.

19. The method of claim 18, wherein dispensing the carrier material into the die chamber comprises forming an active ingredient capsule and/or dispensing the carrier material into the die of the base plate comprises forming a tablet package.

* * * * *